United States Patent [19]
Beljanski

[11] Patent Number: 5,519,028
[45] Date of Patent: May 21, 1996

[54] ANTIVIRAL PREPARATIONS

[76] Inventor: Mirko Beljanski, 46 Boulevard De Port Royal, 75005 Paris, France

[21] Appl. No.: 196,164

[22] PCT Filed: Jul. 26, 1993

[86] PCT No.: PCT/FR93/00761

§ 371 Date: Feb. 22, 1994

§ 102(e) Date: Feb. 22, 1994

[87] PCT Pub. No.: WO94/02146

PCT Pub. Date: Feb. 3, 1994

[30] Foreign Application Priority Data

Jul. 28, 1992 [FR] France ................... 92 09284

[51] Int. Cl.$^6$ ............................. A61K 31/44; A61K 31/47
[52] U.S. Cl. ............................. 514/285; 514/307
[58] Field of Search ..................... 514/285, 307

[56] References Cited

U.S. PATENT DOCUMENTS 5,011,853  4/1991  Olney ....................... 514/454

FOREIGN PATENT DOCUMENTS

| | | |
|---|---|---|
| 0059817 | 9/1982 | European Pat. Off. . |
| 0352147 | 1/1990 | European Pat. Off. . |
| 0373986 | 6/1990 | European Pat. Off. . |
| 2450607 | 10/1980 | France . |
| 679982 | 5/1992 | Switzerland . |

OTHER PUBLICATIONS

Beljanski et al., "Selective Inhibiton of in vitro Synthesis of Cancer DNA by Alkaloids of the β–Carboline Class", Exp. Cell Biol. 50: 79–87 (1982).

Rapaport et al., "Alkaloids of *Geissospermum vellosii*", J. Amer. Chem. Soc. 80: 1601–1604 (1958).

Hughes et al. "Flavopereirine, an Alkaloid from *Geissospermum vellossii*", J. Amer. Chem. Soc. 80: 1604–1609 (1958).

*Primary Examiner*—Shailendra Kumar
*Attorney, Agent, or Firm*—Oppedahl & Larson

[57] ABSTRACT

Flavopereirine taken alone may act as an effective active agent in the struggle against HIV viruses in mammals, including humans. More specifically, it has been found that flavopereirine is an active agent which on its own, whether in vitro or in vivo exerts a selective inhibitlye action on viral HIV infection, particularly in patients infected by HIV-1. Thus, there is provided a method for the treatment of human immunodeficiency virus comprising administering to a human patient infected with human immunodeficiency virus an effective antiviral amount of a composition consisting of flavopereirine or a pharmaceutically acceptable salt or derivative thereof and a pharmaceutically acceptable carrier. The flavopereirine, or one of its salts or other acceptable pharmaceutical derivatives, is preferably administered in solid form containing approximately 250–500 mg of flavopereirine per dose.

9 Claims, 3 Drawing Sheets

ANTIVIRAL PREPARATIONS

BACKGROUND OF THE INVENTION

This invention relates to the antiviral usage of flavopereirine. More specifically, it relates to a pharmaceutical preparation whose sole active ingredient is flavopereirine, and to the use of this preparation for the treatment of viral infections in human—in particular, infections such as those provoked by the Human Immunodeficiency Virus (HIV).

Flavopereirine is an alkaloid of the beta-carboline class. It is also traditionally referred to as "H or PB 100 composition," and shows UV emission fluorescence at 250–254 and 306 nm.

Flavopereirine may be obtained from the peel of the Pao Pereira Geissospermum vellosii-Baillon Apocynaceae (see H. Rapaport et al., J. Amer. Chem. Soc. 80:1601–1608 (1958) and Beljanski et al., request for first certificate of addition #79 05853 to French patent application #78 07155 and EP-A-0 059 817.).

It is known that flavopereirine, administered intracutaneously at a dosage of 200–600 μg or a dosage of 2.5–500 mg/day, preferably 30 mg/day, prevents the appearance and development of vital papules in the case of viruses of the Shope fibrome type and of vaccine.

It is also known that flavopereirine appears to act in vivo against influenza (RNA virus), and that it may moreover inhibit the multiplication of the tobacco mosaic virus (TMV) after brief contact with this virus.

European Patent Application EP-A-0 059 817 reveals that flavopereirine is active against the influenza virus; however, the half-life of a quaternary beta-carboline of this type is too short for efficient use in humans in a galenic form other than time-release capsules.

French Patent Application No. 88 15845 describes a system for improving immune defense in humans (against RNA viruses—AIDS in particular—and DNA viruses). According to this document, the inhibition of the multiplication of the viruses in question is possible only by a combination of four different substances, of which flavopereirine is only one. The pharmaceutical preparation revealed in the document must include at least one representative of each of these four categories of active substances. The flavopereirine included in this combination is administered at a dosage of 0.25 g/day, preferably orally.

SUMMARY OF THE INVENTION

It has now unexpectedly been discovered that flavopereirine taken alone may act as an effective active agent in the struggle against HIV viruses in mammals, including humans. More specifically, it has been found that flavopereirine is an active agent which on its own, whether in vitro or in vivo exerts a selective inhibitive action on viral HIV infection, particularly in patients infected by HIV-1. Thus, in accordance with the present invention there is provided a method for the treatment of human immunodeficiency virus comprising administering to a human patient infected with human immunodeficiency virus an effective antiviral amount of a composition consisting of flavopereirine or a pharmaceutically acceptable salt or derivative thereof and a pharmaceutically acceptable carrier. The flavopereirine, or one of its salts or other acceptable pharmaceutical derivatives, is preferably administered in solid form containing approximately 250–500 mg of flavopereirine per dose.

It is also an object of the present invention to provide a method of using a pharmaceutical preparation based on flavopereirine in order to provide an antiviral treatment for HIV.

A further aspect of the present invention is an article of manufacture comprising a packaging material and a pharmaceutical agent contained within said packaging material, wherein said pharmaceutical agent contains flavopereirine as the sole active ingredient, and wherein said packaging material comprises a label which indicates that the pharmaceutical agent can be used for treatment of human immunodeficiency virus.

DETAILED DESCRIPTION OF THE INVENTION

Flavopereirine has the chemical formula

For use in the present invention, flavopereirine may be prepared by the hydrolysis in 1N HCl of Geissospermum vellosii powder at 100° C., followed by neutralization by KOH, extraction by ethanol and concentration by distillation. The residue of the distillation is subsequently taken up in chloroform, the excess salt is eliminated by precipitation with cold ethanol, and the residue, which contains mainly flavopereirine is concentrated. For purposes of the present invention, the flavopereirine may be used as produced by this process, or can be converted to a pharmaceutically acceptable salt or other derivative.

In accordance with the invention, flavopereirine is administered orally in the forms of capsules to patients infected with HIV at levels of 1–3 grams per day. At this level, flavopereirine is devoid of toxic or side effects in mammals, including humans. Indeed, the $LD_{50}$ in Sprague-Dawley EOPS rats is 10.45 g/kg (safety limits: 9.63–11.35) when administered orally, and 2.45 g/kg (safety limits: 2.35–2.55) when administered intraperitoneally. In determining these values, when the animal died, it died within 30 to 60 minutes of oral or intraperitoneal administration by respiratory arrest. No change in mortality rate was observed during the subsequent 14 days in surviving animals.

Sub-chronic administration in male and female Sprague-Dawley rats (OPA) demonstrated the absence of toxicity in doses equal to 1/20 of the $LD_{50}$ (viz. 530 mg/kg/day), or of 1/5 of the $LD_{50}$ (viz. 2120 mg/kg/day). At these doses, no alterations were noted in either body weight or feeding. Neither was any alteration in the globular blood count noted, and a hepatic and renal functions remained normal. No lesions of the liver, kidneys, duodenum, myocardia, spleen, thyroid and parathyroid glands, testicles or ovaries were visible by microscope.

Flavopereirine was observed to penetrate the blood-brain barrier, as shown by the fact that in male CDI mice which received 10 mg of the flavopereirine preparation orally, the encephalic flavopereirine content was approximately 7 μg (i.e., a concentration of 14 μg/g, from 20 g mice with brains weighing 0.5 g.).

The effectiveness of flavopereirine in the present invention will now be demonstrated by the following non-limiting examples.

EXAMPLE 1

The destruction of HIV by flavopereirine in in vitro cell cultures without effect on normal or healthy cells was demonstrated using the H-9 colony of T4 lymphocytes obtained from Dr. R. Gallo via the Paul Ehrlich Institute (Frankfurt, Germany) and propagated by the Institut fur Medizinische Mikrobiologie und Hygiene (University of Bern, Switzerland).

HIV was obtained as HTLV-III from Dr. Gallo and propagated in the H-9 cells. The surface material produced by the infected H-9 cell culture was stored at −80° C. This material had a concentration of $10^6$ IU/ml at the point of use. The H-9 cells were cultivated in an RPMI 1640 medium containing 15% fetal calf serum, 0.002 μm glutamine and 100 IU penicillin/ml in Falcon flasks (25 cm$^3$). 8 to 20 ml of the medium was used per vial. The vials were incubated at 37° C. in an upright position. The culture was initiated at a concentration of $2\times10^5$ H-9 cells per ml, and divided when the number of cells reached $1\times10^6$ cells/mi. In order to test the flavopereirine in cultures of both infected and non-infected H-9 cells, microtitration plates were used. In these cases, the cultures were begun at a concentration of $6\times10^5$ H-9 cells/mi. After 23 hours incubation, 0.1 ml RPMI 1640 medium containing $10^2$ IU of HIV was added to each well containing 0.1 ml of this cellular suspension. This corresponds to an infection multiplication of $1.6\times10^4$, i.e., one infectious unit per 500 cells. 16 hours after infection, 0.1 ml of RPMI 1640 medium, with or without flavopereirine, was added to the infected and non-infected wells. The flavopereirine was used at a concentration of 30 μg/ml and 60 μg/ml. The microtitration plates were covered with an Amersham plate cover, and incubated at 37° C. Cellular counts were determined using an HIV antigen kit provided by Abbott Laboratories. For purposes of titration, a volume of 10 μl (taken from each of the wells of the microtitration plate) was diluted in 1 ml of RPMI 1640 medium. Based on this stock, 8 dilutions were made in respective series of 1 to 3 and 1 to 5. A volume of 0.1 ml of each dilution was removed and added to 0.2 ml of pre-incubated culture of H-9 cells containing $5\times10^5$ cells/mi. After incubation at 37° C., the presence of HIV antigens was tested using an HIV antigen kit provided by Abbott Laboratories.

Figure 1:
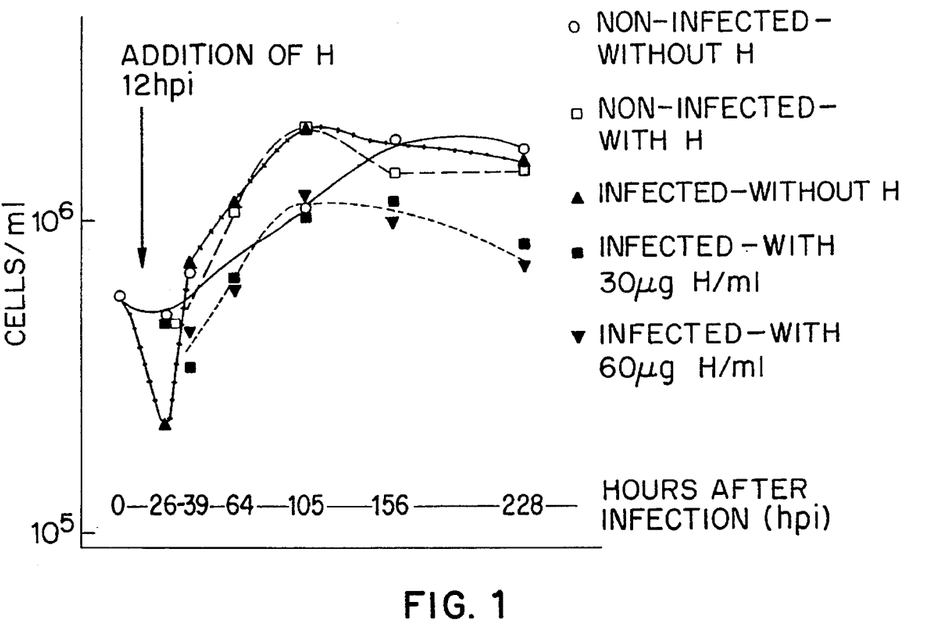
FIG. 1 is a graphic representation of the comparative counts of cells/ml as a function of the number of hours following infection, the addition of flavopereirine (labeled "H") having been made 12 hours after infection.

The results, which are reproduced in graphic form in the attached FIG. 1, show that flavopereirine does not affect the multiplication of non-infected cells. By contrast, the quantity of infected cells is around 40% lower when the flavopereirine is present.

Figure 2:
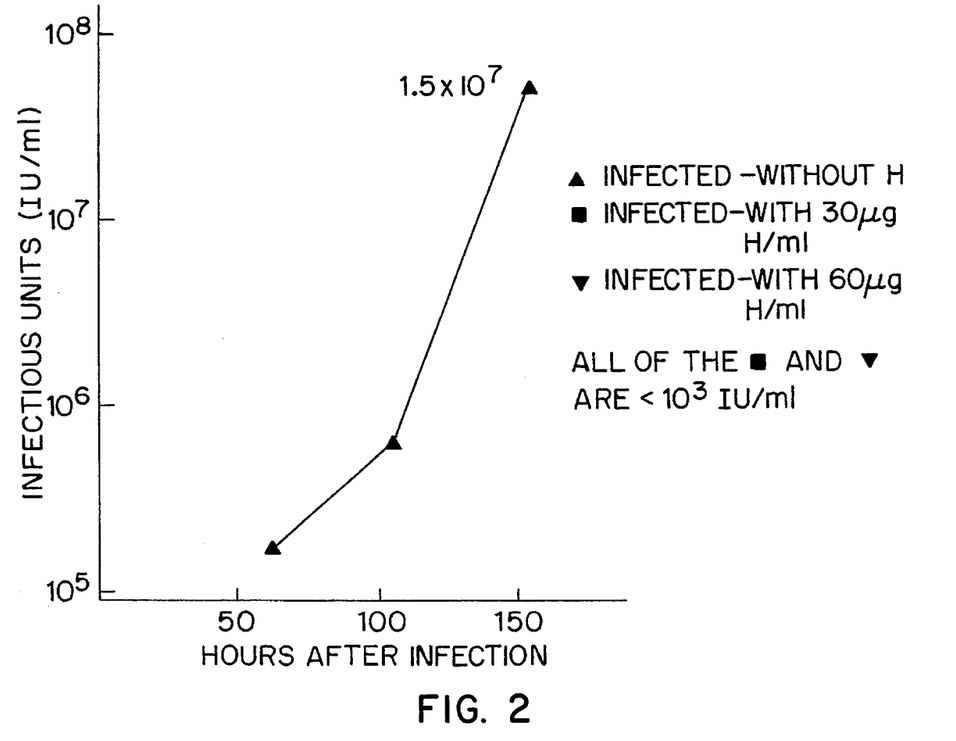
FIG. 2 represents the comparative titre of infectious units (in IU/ml) as a function of the number of hours following infection, without addition of flavopereirine and with addition at levels of 30 and 50 μg/ml.

What was even more striking (as shown in the presentation of results in FIG. 2) was that, although there was an increase in viral particles of untreated infected cells over time, it was not possible, within the limitations of this particular test, to detect the presence of infectious units above 3000 in the series of infected cells treated with flavopereirine (30 μg or 60 μg). This shows that the inhibition of infection exceeds 99% at the very least.

EXAMPLE 2

An evaluation of the antiviral effect of flavopereirine was also undertaken by studying the cytopathogenic effect of the HIV virus on MT4 cells, given that a formation of syncytia was observed 4–6 days after infection by HIV-1, followed by the death of the cells.

The flavopereirine was used in the form of an alcoholic solution (40 mg in 100 μl alcohol). Dilutions were made in RPMI medium at 10% of FCS, 1% of PSN and 1% of glutamine. The MT4 cells were left to pre-incubate for two hours at 37° C. with a successive dilution of flavopereirine containing $3\times10^5$ cells for 10 μl of flavopereirine solution. The solution was obtained by adding 100 μl of a $10^{-4}$ dilution of HIV-1 virus, producing a syncytia formation in 4–6 days. After one hour of incubation at 37° C., the infected MT4 cells were washed three times with RPMI solution before being placed in culture ($3\times10^5$ cells/ml in microplates with 24 wells) with the presence of different dilutions of flavopereirine. The syncytia count was taken each day in duplicate. The results are summarized in tables I, II and III below.

Table I shows cellular toxicity for 100 and 400 μg/ml flavopereirine. At 50 μg/ml syncytia had not formed after 7 days culture. From 10 μg/ml to 100 ng/ml, syncytia was observed, as it was in the HIV-1 control, Table II confirms the protection obtained by flavopereirine at 50 μg/ml, and Table III reconfirms these results: no syncytia were formed at 60 μg/ml after 7 days culture, while a few were observed after 6 days at the dosage 30 μg/ml.

TABLE I

| H | d3 | | d4 | | d6 | d7 |
|---|---|---|---|---|---|---|
| 400 μg/ml | Tox | Tox | | | | |
| 100 | Tox | Tox | | | | |
| 50 | (+) | (+) | (+) | (+) | − | − | − | − |
| 10 | + | + | + | (+) | + | ++ | ++ | ++ |
| 1 | + | (+) | + | + | ++ | ++ | ++/T | ++/T |
| 100 ng/ml | + | + | + | + | ++ | ++ | ++/T | ++/T |
| HIV-1 only | + | + | + | + | ++ | ++ | ++ | ++/T |
| MT4 | − | − | − | − | − | − | − | − |

TABLE II

| H | d3 | d4 | d5 | d6 | d7 | d10 |
|---|---|---|---|---|---|---|
| 100 µg/ml | Tox | Tox | | | | | |
| 50 | – | – | – | – | – | – | – |
| 10 | – | – | + | (+) | + | + | + | ++ | ++ | ++ |
| 1 | – | – | + | + | + | ++ | ++ | ++ | ++ | ++/T |
| 100 ng/ml | – | (+) | + | + | + | + | ++ | ++ | ++ | ++ |
| HIV-1 only | – | – | (+) | + | + | ++ | ++ | ++ | ++/T | ++/T |

TABLE III

| H | d3 | d4 | d5 | d6 | d7 |
|---|---|---|---|---|---|
| 60 µg/ml | – | – | – | – | – | – | – | – | – |
| 30 | – | – | – | – | – | – | (+) | – | ++ | (+) |
| 10 | (+) | – | (+) | (+) | + | (+) | ++ | ++ | ++ | ++ |
| 1 | (+) | (+) | (+) | (+) | (+) | (+) | ++ | + | ++ | ++ |
| 100 ng/ml | – | (+) | (+) | (+) | + | (+) | + | ++ | ++ | ++ |
| HIV-1 only | (+) | (+) | (+) | (+) | + | + | ++ | ++ | ++ | ++ |
| MT4 | – | – | – | – | – | – | – | – | – |

EXAMPLE 3

To test the efficacy of flavopereirine on the infectious capability of HIV-1, two experiments were conducted. In the basic methodology of each experiment, 1 nanogram of primary isolates of HIV-1, BRE1 (from an asymptomatic patient) and TIG2 (from an AIDS patient) were inoculated with $10^6$ peripheral blood mononuclear cells (PBMC) stimulated with PHA taken from five randomly-chosen HIV-negative donors. After 2 hours of incubation, the cells were rinsed twice and cultivated in 1 ml of RPMI 1640 containing 20 IU of IL-2 per ml (Boehringer Mannhelm, Germany), 2 µg of Polybrene (hexadimethrine bromide) per ml (Sigma, St. Louis, Mo., USA) and $10^{-7}$ IU of goat antiserum acting against human alpha interferon (Janssen, Beerse, Belgium) per ml. Half the culture was changed after 72 hours, and thereafter every 48 hours until the 30th day.

For the first experiment, prior to incubation of the virus in PBMC stimulated by PHA (blast cells), extracellular viral stocks were pretreated in triplicate with 30 or 60 µg flavopereirine per ml for two hours. In the second experiment, blast cells were pretreated in triplicate with 30 or 60 µg flavopereirine per ml for two hours, and were then rinsed twice before exposure to the viral inoculum.

The surface material of the culture was tested by an immuno-enzymatic (ELISA) assay for the production of antigen P24 (Abbott, Chicago, Ill., USA) and the optical density (OD) of the resulting color was converted into P24 concentration from the slope of a standard nomogram, as described by W. Lu and J. -M. Andrieu, Journal of Virology, 66(1): 334–340 (1992). The result of the two experiments are shown in Tables IV and V, respectively. As shown, a pretreatment of HIV-1 by flavopereirine (compound H) at a level of 30 or 60 µg/ml completely prevented the infection of target PBMC by primary HIV-1 isolates taken from both symptomatic and asymptomatic patients. On the other hand, only pretreatment of target PBMC with 60 µg/ml led to complete inhibition of productive viral infections.

EXAMPLE 4

To evaluate the cytotoxicity of flavopereirine in resting PBMC and in blast cells, prewashed fresh and blastic PBMC taken from five randomly-selected, healthy, HIV-negative donors were treated in triplicate with 30 or 60 µg flavopereirine per ml of alcoholic solution for two hours, After washing twice, the cells were placed in culture in cellular culture medium until day 15. The viability of the cells of each group was examined by exclusion coloring with trypan blue and by quantimetric analysis. Cultures of HIV-negative PBMC without flavopereirine (compound H) were used as controls. The results are summarized in Table VI. As shown, the viability of resting PBMC was reduced significantly ($p<0.05$) in the group of cells treated with 60 µg/ml, but this was not the case in the group treated with 30 µg of compound H per ml. Viability of the blastic cells appeared to be independent of exposure to compound H.

EXAMPLE 5

To further test the inhibition of productive infection by HIV-1 through use of flavopereirine, HIV-1 was pretreated with flavopereirine (compound H) in doses of 10, 30, 60, 100, 200 µg/ml and then combined with PBMC. Flavopereirine was found to inhibit infection of target PBMC by the virus in a manner dependent on the dose (see Table VII below). Doses equal to or higher than 60 µg of compound H per ml appeared to represent the required concentration for complete inhibition of productive viral infections.

This experiment was repeated, but prior to the pretreatment the virus was combined with human serum. In the primary human PBMC culture system, the efficacy of flavopereirine (compound H) on the inhibition of wild HIV-1 remained unchanged when the medicine was placed for incubation in a culture medium containing 50% human serum before the inhibition experiment. (See Table VIII).

EXAMPLE 6

The cytotoxicity of flavopereirine (compound H) in human PBMC stimulated with PHA was tested in the presence and absence of human AB serum as shown in Table IX. These tests showed that the viability of blast PBMC diminished significantly ($p<0.001$) in the group of cells treated with 200 µg/ml, but this was not the case in the groups treated with 100, 60, 30 and 10 µg/ml compound H respectively. Thus, the replication of HIV-1 can be totally inhibited by a concentration of flavopereirine (60–100 µg/ml) that is 2 to 4 times weaker than the cytotoxic concentrations. This effect did not appear to be influenced by the constituents of the human serum.

EXAMPLE 7

The effects of flavopereirine on the production of primary (IL-1β and TNF-α) and secondary (IL-6) cytokines by monocytes was also tested. The adhesive monocytes used were taken from the blood of two types of donors:

Normal donors—voluntary blood donors who attended the blood bank of the Pitié-Salpêtrière Hospital, Paris, France; and HIV-positive donors from medical consultations. These individuals were in the early stages of HIV infection and, at the moment of taking the blood, were not undergoing any treatment. The risk factors involved were intravenous drug abuse for six of the donors, sexual transmission for three and blood transfusion (in Zaire) for one patient. No correlation was found between the risk factors and the results of the experiments.

In the case of the HIV-positive donors, a number of anomalies were found; these related mainly to the polynuclear and lymphocytic lines;

Hypersegmented or hyposegmented (Pelger type) polynuclears in four cases out of 10.

Hyperbasophilic lymphocytes were also found in four cases out of 10 (not the same cases as the above). No correlation was found between these anomalies and the results obtained in the experiments.

In immunophenotypical analysis, no expression of the differentiation antigens (CD34, CD33, CD13 and CD11$b$) examined was found deficient.

I. Normal donors

The ten donors in these experiments showed a considerable coherence of results;

No spontaneous production of either primary cytokines (IL-Iβ and TNF-α) or of interleukin-6, a secondary cytokine;

The stimulation of monocytes over a period of 48 hours with interferon (1000 U/ml) did not cause any production of primary cytokines, except in donor #10 in 1L-1β, or of secondary cytokine, except for donors #1 and 5.

As expected, the stimulations obtained with LPS (lipopolysaccharide) and the combination interferon-γ+ LPS they varied in amplitude from donor to donor; they were always significant, with a synergic effect in the case of double stimulation.

Effect of product H

Product H was not used in these experiments at a rate of more than 20 μg/ml water, since above this rate, net toxicity could have been produced. Four donors were previously tested with 30, 50, 100 μg/ml with virtually total cytotoxicity: above 40% at 30 μg/ml, and 100 μg/ml above that rate (analysis of the culture surface material was not prepared).

The doses of 5, 10 and 20 μg/ml were chosen from the second series of experiments onwards, after the results from the first two donors had shown that doses of less than 5 μg/ml proved inactive.

Direct activity of product H

On the production of primary cytokines:

* Increase in the production of TNF-α (donor 7), in one dose only; this effect was also detected in the response to IFN-γ.

* Increase in the production of IL-1β (donors #3, 5 and 6) with a dose effect, though this was marginal. Donor #10, however, responded very well to doses of 10 and 20 μg/ml.

On the production of secondary cytokine (interleukin-6):

* No modification in response was observed.

Indirect Activity of product H

On the production of primary cytokines:

* Production of TNF-α: There was a sharp reduction in production, but solely in the case of a heavy dosage of the product (20 βg/ml) ($p<0.05$).

* Production of IL-1β: there was no significant modification of the responses to LPS or to IFN-γ+LPS ($p<0.05$).

On the production of secondary cytokine (interleukin-6):

* There was a sharp reduction in the production of IL-6; this inhibition was never total, and, contrary to the case of TNF-α, it was dose-dependent ($P<0.05$).

Figure 3:
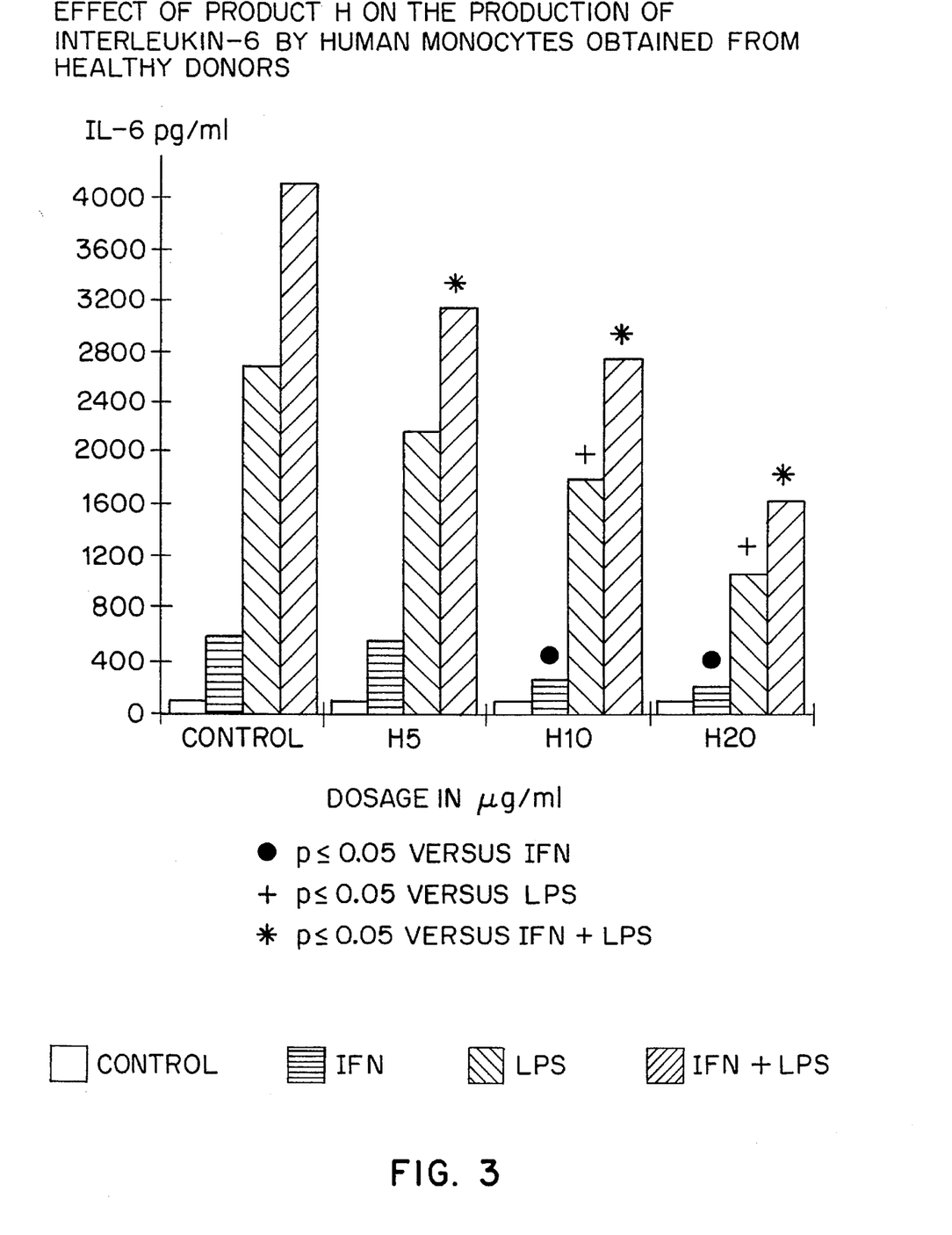
FIG. 3 represents in diagrammatic form the effect of flavopereirine on the production of interleukin-6 by human monocytes from healthy donors.
Figure 4:
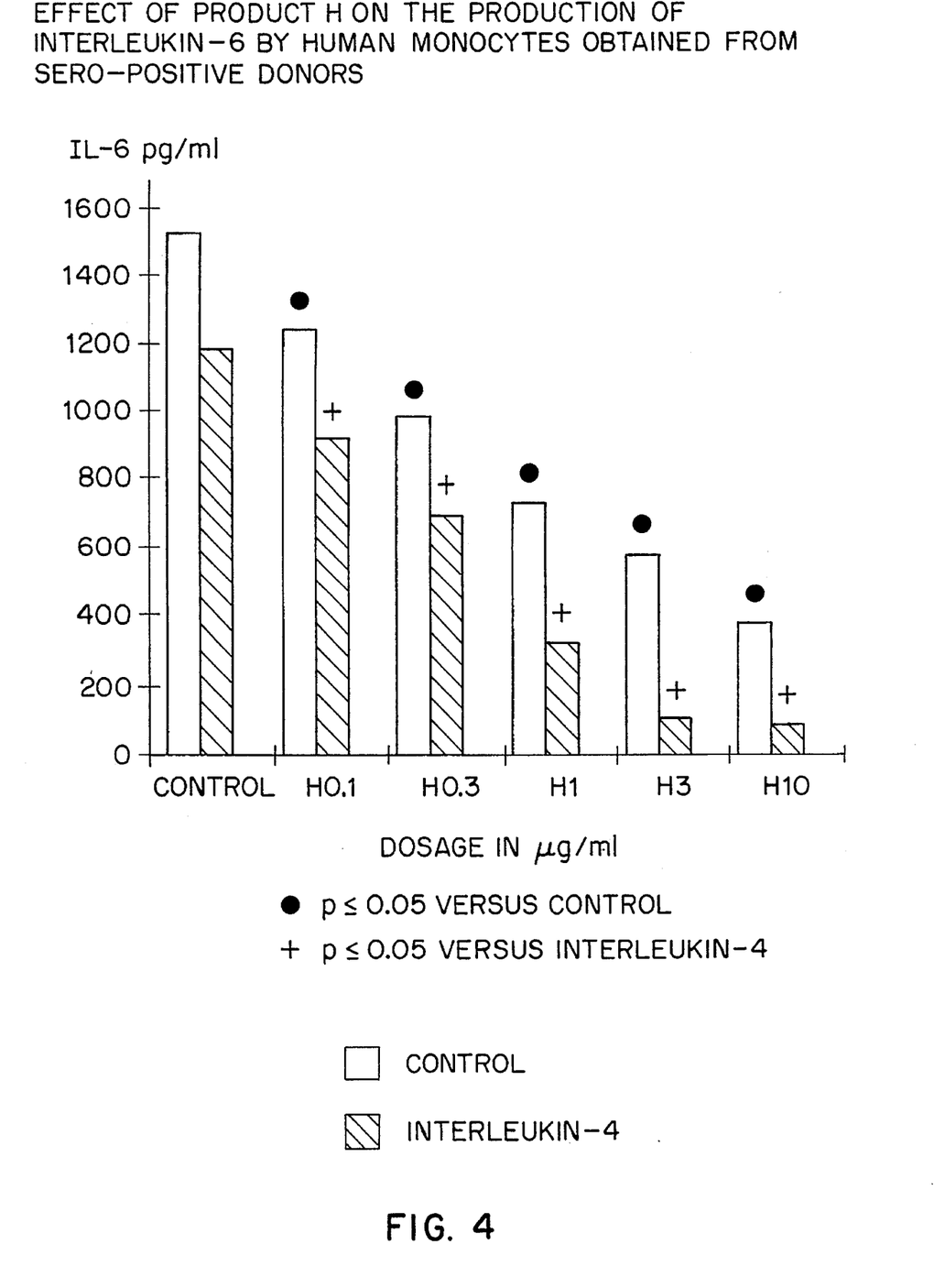
FIG. 4 represents in diagrammatic form the effect of flavopereirine on the spontaneous production of interleukin-6 by human monocytes taken from HIV-positive patients.

These different results are organized in diagrams 3 and 4, in which the measured doses are shown in μg/ml of cytokines, and the standard deviations are not precise, since these are always 10% less than the average.

II. HIV-positive donors

The response of the monocytes taken from the various HIV-positive donors was tested in terms of spontaneous response. The quantities of cells received were low (the donors were not affected by cytapheresy), and the experiments were therefore limited by the number of cells available.

Direct activity of product H

On the production of primary cytokines.

No modification on the base production was observed, whether for TNF-α or for IL-1β.

On the production of secondary cytokine.

8 out of 10 donors showed a significant spontaneous response in interleukin-6.

Indirect activity of product H

Effect on the production of primary cytokines.

The effects obtained were the same as those for healthy donors, namely an almost total reduction in the production of TNF-α (only at a dosage of 20 μg/ml) and an absence of any impact on the production of interleukin-1 at the three dosages employed ($p<0.05$).

Effect on the production of interleukin-6.

Interleukin-4 was used at the same time as flavopereirine H, since it has been shown prior to these experiments that this cytokine blocks the spontaneous production of interleukin-6 in certain HIV-positive patients.

In five cases, interleukin-9 was used for comparison, since this, too, blocks the production of IL-6 in normal monocytes stimulated by LPS.

The results obtained were as follows:

* Interleukin-4 inhibited the production of IL-6, but this inhibition was never total ($p<0.05$).

* Interleukin-9 partially inhibited (up to a maximum of 50%) spontaneous production; it never has a compound effect to that of interleukin-4 (indeed, in two out of five cases, it caused the neutralization of these effects; these results are not shown in the tables).

* Product H showed an inhibitory effect with a very clear dosage effect ($p<0.05$). However, it never led to the total inhibition of the spontaneous production of IL-6. On the contrary, in the presence of interleukin-4, an amplification effect was almost always obtained (except in case #4), with total disappearance of production at 3 µg/ml of product H (and often even from 1 µg/ml) (p<0.05).

In conclusion:

Product H proved toxic at dosages higher than 20 µg/ml in vitro on the cells used within the framework of these experiments, viz. human monocytes taken both from healthy and from asymptomatic HIV-positive donors;

Product H proved able to modulate the production of cytokines: this was true directly for primary cytokines, though this effect was weak; indirectly, this modification was marked in the case of the production of TNF-α and IL-6, though not IL-1. Product H also inhibited the spontaneous production of IL-6 shown in some HIV-positive patients. This inhibitory effect, which in these experiments was never total, was amplified in the presence of IL-4;

The normalization of the IL-6 and TNF-α responses in the HIV positive subject, except for the inhibition of the production of IL-1, was highly significant, since product H did not modify the potential immune relations between monocytes and lymphocytes, or the majority of the inflammatory reactions necessary for survival, such as the stimulation of the stock cells of the bone marrow and the establishment of a defense reaction on the general level.

EXAMPLE 8

To test the clinical tolerance and efficacy of flavopereirine a clinical study was carried out on 24 HIV-positive patients with total T4 lymphocyte counts at absolute values ranging from $0.2-0.4 \times 10^9/l$. All the patients were informed about the active ingredient being used and about the other antiretrovirus medicines in use at the time of the study. The selection of patients was made on the basis of the absolute T4 lymphocyte count: men and women above 18 years of age, having a Karnofsky index equal to or higher than 90%, showing presence of anti-HIV I antibodies in two successive tests (ELISA method), from groups CDC II, CDC III, CDC IV C2, CDC IV E in the CDC 87 classification; with hemoglobin higher than 100–120 g/l, neutrophile polynuclears higher than $1.5 \times 10^9/l$, platelets numbering more than $80 \times 10^9/l$, T4 lymphocytes numbering no more than $0.2 \times 10^9/l$ and no less than $0.4 \times 10^9/l$, and the absence of anti-retroviral therapy, particularly by AZT.

20 patients were accepted on the basis of the above criteria. Before inclusion in the study, a pretherapeutic study was made for each patient: postclinical and therapeutic history, clinical examination including determination of fever, anorexia and nausea, headaches, pruritus, cough and expectoration, diarrhea, adenopathies, buccal mycoses, seborrheic dermatitis and Kaposi's lesions. A biological study was also undertaken; this included red corpuscles, platelets, lymphocytic sub-groups (CD2, CD4, VDS, CD19, CD4/8), determination of antigen P24 and microglobulin beta-2, of DHL (dehydrogenated lactate), plasmatic ferritin, ALAT (alanine-amino-transferase), ASAT (aspartate-aminotransferase) and plasmatic creatinine.

The flavopereirine (compound H) was administered in the form of 600 mg capsules, at a daily dose of 1–3 g, preferably at least around 1 g, which is generally active for one day, The average length of treatment was 43 ±11 weeks. Side effects were few, occurring only in the first three months. Neither blood nor renal toxicity was observed; nor was there any significant modification in ALAT or ASAT. No degradation in the CDC classification and no infections were noticed; the Karnofsky's index remained around the 100% level in all cases- Physical and professional activity on the part of the patients remained completely normal.

Immune response to the treatment was expressed mainly in a significant increase in CD4+ cells (p.<0.05), as well as in CD19+ cells (p<0.05). The negative decline in CD4+ was reversed in 18 out of 19 patients (p<0.05).

All the in vitro and in vivo results clearly indicate that the flavopereirine compound exerts a significant inhibitory effect on the viral infectional capacity of HIV, both in vitro in human cells and in vivo in HIV-1 infected patients.

In 10 of the patients treated over a year, the following significant variations were further noted:

Increase in red cells at 9 months;

Increase in hemoglobin at 9 months;

Increase in the total lymphocyte mass at 9 and 12 months;

Increase in CD2 at 9 months;

Increase in CD4 at 12 months;

Increase in CD8 at 9 months;

Increase in CD19 at 6–9 and 12 months;

Increase in microglobulin beta-2 at 3–6 and 12 months.

In practice, oral administration in solid form, such as tablets or capsules, for example, is recommended. A unitary dosage of around 250–500 mg of active ingredient is particularly appropriate.

The recommended dosage, in the light of the above results and the indications of toxicity, is around 1–3 g, which are generally active for one day (g/d) and preferably at least around 1 g/d, most profitably taken at successive intervals over the course of the day.

The dosages and/or galenic forms retained may, however, vary according to the state of the patient and the stage of viral attack being treated. Their adaptation to the specific case concerned in each particular treatment may be easily achieved by the professional on the basis of his relevant experience and, if necessary, with the assistance of routine preliminary tests. In this respect, it is particularly recommended that close attention be paid to the data provided by a pharmacokinetic study of the patient made in order to establish the half-life, of the active ingredient being administered, and, if necessary, to adapt the form of pharmaceutical preparation for administration accordingly. The latter may, for example, take the form of time-release galenic preparations.

Apart from the active ingredient or a salt or other derivative thereof, the doses for administration include at least one pharmaceutical support or vector, as well as excipients, carriers and standard perfumes and/or colorants.

TABLE IV

Pretreatment of viral inoculum with compound H (experiments in triplicate)

| Viral stock (1 ng/ml) | HIV pretreated with H for 2 hours | Post-infection production of HIV P24 (pg/ml) | | | | |
|---|---|---|---|---|---|---|
| | | d3 | d5 | d14 | d21 | d30 |
| HIV-1$_{Asym.}$ (Stock$_{Brat}$) | Control | 250 ± 25 | >1500 | | | |
| | + 30 µg/ml | – | – | – | – | – |
| | + 60 µg/mi | – | – | – | – | – |
| HIV-1$_{AIDS}$ (Stock$_{Tigr}$) | Control | 575 ± 129 | >1500 | | | |
| | + 30 µg/ml | – | – | – | – | – |
| | + 60 µg/ml | – | – | – | – | – |

Reunified peripheral blood mononuclear cells (PBMC) taken from five randomly-chosen, healthy, HIV-negative donors.

TABLE V

Pretreatment of target cells with compound H (experiments in triplicate)

| Viral stock (1 ng/ml) | PBMC* pretreated with H for 2 hours | Post-infection production of HIV P24 (pg/ml) | | | | |
|---|---|---|---|---|---|---|
| | | d3 | d5 | d14 | d21 | d30 |
| HIV-1<sub>Asmy.</sub> (Stock<sub>Brat</sub>) | Control | 250 ± 25 | >1500 | | | |
| | + 30 µg/ml | 113 ± 7 | >1500 | | | |
| | + 60 µg/ml | – | – | – | – | – |
| HIV-1<sub>AIDS</sub> (Stock<sub>Tigr</sub>) | Control | 575 ± 129 | >1500 | | | |
| | + 30 µg/ml | 515 ± 103 | >1500 | | | |
| | + 60 µg/ml | – | – | – | – | – |

*Reunified PBMC taken from five randomly-chosen, healthy, HIV-negative donors.

TABLE VI

Cytotoxicity of compound H in human PBMC at rest and in PBMC stimulated by PHA (blastic) (experiments repeated 5 times)

| Target cells | Cells treated with H (2 hrs.) | Viability (%) of PBMC after exposure to compound H | | | | |
|---|---|---|---|---|---|---|
| | | d3 | d7 | d11 | d13 | d15 |
| PBMC* | Control | 97 ± 2 | 95 ± 3 | 98 ± 2 | 91 ± 8 | 85 ± 9 |
| | + 30 µg/ml | 95 ± 4 | 93 ± 2 | 88 ± 7 | 82 ± 10 | 81 ± 11 |
| | + 60 µg/ml | 56 ± 6 | 23 ± 4 | 17 ± 4 | 12 ± 5 | 25 ± 8 |
| Blast.** | Control | 86 ± 5 | 34 ± 6 | 76 ± 4 | 75 ± 5 | 68 ± 7 |
| | + 30 µg/ml | 88 ± 3 | 35 ± 7 | 71 ± 3 | 76 ± 9 | 69 ± 8 |
| | + 60 µg/ml | 79 ± 4 | 74 ± 5 | 70 ± 4 | 71 ± 8 | 63 ± 7 |

*Reunified PBMC taken from five randomly-chosen, healthy, HIV-negative donors.
**Blastic cells stimulated with PHA taken from five randomly-chosen, healthy, HIV-negative donors.

TABLE VII

Pretreatment of viral inoculum with compound H in the absence of human AB group serum (experiment repeated 5 times)

| HIV pretreated with H for 2 hrs. | Production of P24 in HIV (pg/ml) | | | |
|---|---|---|---|---|
| | d4 | d10 | d14 | d21 |
| Control | 510 ± 235 | >1500 | | |
| + 200 µg/ml | – | – | – | – |
| + 100 µg/ml | – | – | – | – |
| + 60 µg/ml | – | – | – | – |
| + 30 µg/ml | 173 ± 102 | >1500 | | |
| + 10 µg/ml | 388 ± 124 | >1500 | | |

Reunified peripheral blood mononuclear cells (PBMC) taken from five randomly-chosen, healthy, HIV-negative donors.

TABLE VIII

Pretreatment of viral inoculum with compound H in the presence of human AB serum (experiment repeated 3 times)

| HIV pretreated with H for 2 hrs. | With/w.out (–/+) 50% of AB serum | Production of P24 in HIV (pg/ml) | | | |
|---|---|---|---|---|---|
| | | d4 | d10 | d14 | d21 |
| Control | – | 510 ± 235 | >1500 | | |
| + 200 µg/ml | + | – | – | – | – |
| + 100 µg/ml | + | – | – | – | – |
| + 60 µg/ml | + | – | – | – | – |
| + 30 µg/ml | + | 275 ± 98 | >1500 | | |
| + 10 µg/ml | + | 384 ± 83 | >1500 | | |

Reunified peripheral blood mononuclear cells (PBMC) taken from five randomly-chosen, healthy, HIV-negacive donors.

TABLE IX

Cytotoxicity of compound H on human PBMC stimulated with PHA (blasts) in the presence or absence of human AB group serum (experiment repeated 5 times)

| Cells treated with H (2 hrs.) | With/w.out (–/+) 50% of AB serum | Cytotoxicity of compound H after exposure to PBMC* | | | |
|---|---|---|---|---|---|
| | | d4 | d10 | d14 | d21 |
| Control | – | 85 ± 1.4** | 86 ± 1.3 | 80 ± 2.7 | 77 ± 3.1 |
| + 200 µg/ml | – | 45 ± 6.3 | 33 ± 7.8 | 24 ± 7.6 | 15 ± 5.4 |

TABLE IX-continued

Cytotoxicity of compound H on human PBMC stimulated with PHA
(blasts) in the presence or absence of human AB group serum
(experiment repeated 5 times)

| Cells treated with H (2 hrs.) | With/w.out (−/+) 50% of AB serum | Cytotoxicity of compound H after exposure to PBMC* | | | |
|---|---|---|---|---|---|
| | | d4 | d10 | d14 | d21 |
| + 100 µg/ml | − | 84 ± 1.6 | 79 ± 3.1 | 73 ± 5.3 | 74 ± 4.7 |
| + 60 µg/ml | − | 86 ± 1.5 | 82 ± 2.4 | 82 ± 2.6 | 80 ± 3.3 |
| + 30 µg/ml | − | 81 ± 2.8 | 83 ± 2.6 | 80 ± 3.9 | 78 ± 4.8 |
| + 10 µg/ml | − | 87 ± 1.2 | 86 ± 1.4 | 84 ± 1.5 | 81 ± 2.3 |
| + 200 µg/ml | + | 37 ± 6.8 | 24 ± 6.6 | 17 ± 7.9 | 11 ± 5.6 |
| + 100 µg/ml | + | 83 ± 2.3 | 80 ± 4.5 | 77 ± 5.6 | 73 ± 4.4 |
| + 60 µg/ml | + | 85 ± 1.2 | 84 ± 1.7 | 82 ± 2.1 | 79 ± 3.5 |
| + 30 µg/ml | + | 88 ± 1.3 | 84 ± 2.5 | 82 ± 3.7 | 81 ± 4.6 |
| + 10 µg/ml | + | 87 ± 1.1 | 88 ± 1.4 | 84 ± 3.2 | 82 ± 3.1 |

*Blastic cells stimulated with PHA taken from five randomly-chosen, healthy, HIV-negative donors.
**Percentage (average ± standard deviation) viable cells

I claim:

1. A method for the treatment of human immunodeficiency virus comprising administering to a human patient infected with human immunodeficiency virus an effective antiviral amount of a composition consisting of flavopereirine or a pharmaceutically acceptable salt or derivative thereof and a pharmaceutically acceptable carrier.

2. A method according to claim 1, wherein the flavopereirine is administered orally at a level of 1 to 3 grams per day.

3. A method according to claim 2, wherein the flavopereirine is administered in a solid form containing 250–500 mg flavopereirine.

4. A method according top claim 2, wherein the flavopereirine is formulated as a tablet or capsule.

5. A method according to claim 4, wherein the flavopereirine is formulated in a time-release galenic form.

6. A method according to claim 1, wherein the flavopereirine is formulated in a time-release galenic form.

7. A method according to claim 1, wherein the flavopereirine is obtained by extraction from the root of Pao Pereira Geissospermum vellosii-Baillon.

8. A pharmaceutical composition in dosage unit form consisting of 250–500 mg of flavopereirine per dose in a pharmaceutically acceptable carrier.

9. A pharmaceutical composition according to claim 8, wherein the flavopereirine is formulated in a time-release galenic form.

* * * * *